United States Patent
Dang et al.

(10) Patent No.: US 9,707,336 B2
(45) Date of Patent: Jul. 18, 2017

(54) PRIMING DETECTION SYSTEM AND METHOD OF USING THE SAME

(71) Applicant: Medtronic MiniMed, Inc., Northridge, CA (US)

(72) Inventors: Kiem H. Dang, Thousand Oaks, CA (US); Edgardo C. Halili, Santa Clarita, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 118 days.

(21) Appl. No.: 14/246,982

(22) Filed: Apr. 7, 2014

(65) Prior Publication Data

US 2015/0283321 A1   Oct. 8, 2015

(51) Int. Cl.
| | |
|---|---|
| *A61M 1/00* | (2006.01) |
| *A61M 5/142* | (2006.01) |
| *A61M 5/162* | (2006.01) |
| *A61M 5/14* | (2006.01) |

(52) U.S. Cl.
CPC ...... *A61M 5/14244* (2013.01); *A61M 5/1626* (2013.01); *A61M 2005/1402* (2013.01); *A61M 2205/583* (2013.01)

(58) Field of Classification Search
CPC .... A61M 5/14; A61M 5/142; A61M 5/14244; A61M 5/145; A61M 5/158; A61M 5/162; A61M 5/3146; A61M 2005/1401; A61M 2005/1402; A61M 2205/584; A61M 5/3213

USPC ...... 604/111, 131, 151, 164.01, 164.08, 192, 604/197

See application file for complete search history.

(56) References Cited

U.S. PATENT DOCUMENTS

| | | | |
|---|---|---|---|
| 4,114,617 A * | 9/1978 | Turner | A61M 5/1408 604/186 |
| 4,755,173 A | 7/1988 | Konopka et al. | |
| 5,147,309 A * | 9/1992 | Hemmerich | A61M 5/002 604/122 |
| 5,391,250 A | 2/1995 | Cheney, II et al. | |
| 5,485,408 A | 1/1996 | Blomquist | |
| 5,522,803 A | 6/1996 | Teissen-Simony | |
| 5,665,065 A | 9/1997 | Colman et al. | |
| 5,800,420 A | 9/1998 | Gross et al. | |
| 5,807,375 A | 9/1998 | Gross et al. | |

(Continued)

*Primary Examiner* — Edelmira Bosques
(74) *Attorney, Agent, or Firm* — Medtronic Minimed, Inc.

(57) ABSTRACT

An infusion system having a priming detection system to indicate that a component of the system, for example a cannula or needle, is primed with a fluid to be delivered into an individual's body. The infusion system utilizes a reactive element that reacts with the fluid or at least one component of the fluid to be delivered, to produce a color change or a colored complex. The reactive element can be deposited, coated or otherwise incorporated in any component of the infusion system that would benefit from a visible indication of a primed fluid, including, but not limited to a tubing, infusion set, cannula, needle and/or guard element at least partially covering or surrounding a cannula or needle. The visual indication improves the user experience during the priming and filling of the system by providing a clear color change confirmation upon priming completion and prior to insertion into the body.

19 Claims, 11 Drawing Sheets

(56) References Cited

U.S. PATENT DOCUMENTS

| | | | |
|---|---|---|---|
| 5,855,896 A * | 1/1999 | Lim | A61M 5/32 252/408.1 |
| 5,925,021 A | 7/1999 | Castellano et al. | |
| 5,954,643 A | 9/1999 | Van Antwerp et al. | |
| 5,958,404 A * | 9/1999 | Selawry | A61K 35/12 424/93.7 |
| 6,017,328 A | 1/2000 | Fischell et al. | |
| 6,059,758 A * | 5/2000 | Padilla | A61M 5/3213 604/192 |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,461,329 B1 * | 10/2002 | Van Antwerp | A61M 5/16836 604/111 |
| 6,544,212 B2 | 4/2003 | Galley et al. | |
| 6,558,351 B1 | 5/2003 | Steil et al. | |
| 6,591,876 B2 | 7/2003 | Safabash | |
| 6,641,533 B2 | 11/2003 | Causey, III et al. | |
| 6,736,797 B1 | 5/2004 | Larsen et al. | |
| 6,749,587 B2 | 6/2004 | Flaherty | |
| 6,752,785 B2 | 6/2004 | Van Antwerp et al. | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,602,310 B2 | 10/2009 | Mann et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 2007/0123819 A1 | 5/2007 | Mernoe et al. | |
| 2008/0051714 A1 * | 2/2008 | Moberg | A61M 5/1413 604/135 |
| 2008/0118397 A1 * | 5/2008 | Slowey | A61B 10/0051 422/400 |
| 2010/0160861 A1 | 6/2010 | Causey, III et al. | |
| 2010/0190251 A1 * | 7/2010 | Kim | C12N 5/0676 435/377 |
| 2011/0071492 A1 * | 3/2011 | Horvath | A61M 5/326 604/506 |
| 2014/0374353 A1 * | 12/2014 | Wright | A61M 1/342 210/646 |

\* cited by examiner

PRIMING DETECTION SYSTEM AND METHOD OF USING THE SAME

FIELD OF THE INVENTION

This invention relates to a fluid infusion system having a priming detection system, and in particular embodiments, one or more components of a fluid infusion system having a reactive element that provides a color change upon contact with an infusion fluid to indicate the completion of priming of the infusion system.

BACKGROUND OF THE INVENTION

Continuous subcutaneous infusion of medications is a prevalent method of drug delivery. Typically, an individual uses a small programmable pump to deliver medication through a flexible plastic tube to an infusion set. The infusion set delivers medication to an individual's subcutaneous tissue through the use of either a rigid needle that is left in the tissue or through a flexible cannula that remains in the tissue after being inserted via a removable needle. The most common infused fluid is insulin. An estimate of over 500,000 individuals worldwide use subcutaneous infusion of insulin for the treatment of diabetes mellitus. However, other infused fluids include HIV drugs, drugs to treat pulmonary hypertension, iron chelation drugs, pain medications, and anti-cancer treatments.

An insulin delivery system generally includes a pump, tubing and infusion set attached to a cannula or needle. The tubing is connected to the pump at one end and connected to the cannula or needle at the other end to deliver the insulin into the body. During the initial set up of the system, the user executes a priming sequence to fill the tubing and cannula or needle with insulin prior to insertion of the cannula or needle into the body.

Existing methods of detecting whether the tubing and cannula or needle is primed with insulin require the user to watch for droplets of insulin forming on the tip of the needle. This method of detection can be challenging for those who have poor vision, especially the elderly and diabetics with impaired vision. In addition, infusion systems can include a needle guard to cover the needle and prevent accidental poking of oneself. Such systems require removal of the needle guard to allow the user to view the insulin droplet form at the tip of the needle during the priming sequence of the pump. Current infusion systems do not provide a noticeably clear method to observe completion of priming without straining the eyesight and/or compromising the safety of the user.

BRIEF SUMMARY OF THE INVENTION

Embodiments of the present invention include a priming detection system and method for clear visual confirmation that a component of an infusion system is primed with an infusion fluid, which obviate for practical purposes, the above mentioned limitations.

According to an embodiment of the invention, the infusion system includes at least one reactive element to react with a fluid to be delivered into an individual's body. In embodiments, the reactive element reacts with the fluid or a component within the fluid when the fluid contacts the reactive element to produce a color change. The color change indicates that the component of the infusion system is primed with the fluid. In embodiments, the delivered fluid can be a therapeutic agent such as insulin or any other suitable medicament.

In embodiments, the system can further include a delivery element, such as a cannula or needle. The delivery element can have a proximal end and a distal end. The distal end of the delivery element can be configured to penetrate the individual's body and the proximal end of the delivery element can be directly or indirectly connected to the delivery device, to provide fluid communication between the delivery device and the individual's body so that the fluid can travel from the delivery device through the delivery element into the individual's body. In some embodiments, the reactive element is deposited on or incorporated in at least a portion of the delivery element.

According to another embodiment of the invention, the system further includes a guard element to at least partially surround or cover at least a portion of the delivery element. In some embodiments, the guard element includes at least one reactive element that reacts with the fluid exiting from the delivery element to produce a color change to indicate that the delivery element is primed with the fluid. In some embodiments, the guard element has an interior surface and an exterior surface and the reactive element is deposited on at least a portion of the interior surface of the guard element. In alternative embodiments, the reactive element can be incorporated into the material comprising the guard element.

In embodiments, the infusion system further includes a device for delivering the fluid into the individual's body. The delivery device can be an infusion pump, an infusion set, or another suitable fluid delivery device or fluid source. In some embodiments, the infusion pump is coupled to the delivery element. In further embodiments, the infusion set is coupled to the delivery element. In yet further embodiments, the system can include a tube coupled between an infusion set and an infusion pump, and/or between the delivery element and the delivery device, such as an infusion set or infusion pump. In embodiments including the tube, at least one reactive element can be deposited within at least a portion of the tube.

In embodiments, at least one reactive element can be applied to or incorporated in one or more components of the infusion system. In further embodiments, at least one reactive element is encapsulated in micro-spheres. In yet further embodiments, at least one reactive element is a component of a coating.

In one particular embodiment, the invention is a fluid detection system having at least one reactive element to indicate a component of an infusion system is primed with a fluid to be delivered into an individual's body. The fluid detection system comprises a delivery element having a proximal end and a distal end, the distal end configured to penetrate the individual's body and the proximal end coupled to a fluid source. For example, the fluid source can be an infusion set and/or an infusion pump. In embodiments, the fluid detection system further includes a guard element having a body that surrounds at least a portion of the delivery element. The guard element includes at least one reactive element that reacts with the fluid exiting from the distal end of the delivery element to produce a color change to indicate that the delivery element is primed with the fluid.

In embodiments, at least one reactive element is a liquid-activated dye to produce the color change when the fluid contacts the dye. For example, in some embodiments the liquid activated dye is a reversible or irreversible hydrochromatic or hydrochromic ink or dye. In further embodiments, at least one reactive element includes a chemical that reacts with at least one component within the fluid to produce the color change. For example, in some embodiments, at least one reactive element contains at least 4-amino-antipyrine and potassium ferricyanide. In alternative embodiments, at least one reactive element contains at least 4-amino-antipyrine, potassium ferricyanide and horse radish peroxidase (HRP). In another embodiment, at least one reactive element contains at least ninhydrin. In yet another embodiment, at least one reactive element contains at least Coomassie Brilliant Blue. In a further embodiment, at least one reactive element contains dithizone.

Various methods for determining when a component of an infusion system is primed with a fluid to be delivered into an individual's body can be ascertained from the description of embodiments of the invention herein. In one embodiment, the method comprises: providing the fluid and a device for delivering the fluid into the individual's body; providing the delivery element having a proximal end and a distal end, the distal end configured to penetrate the individual's body and the proximal end connected to the delivery device; providing a guard element to cover at least the distal end of the delivery element; depositing at least one reactive element that reacts with the fluid on the guard element; and producing and/or observing a color change when the fluid exiting from the distal end of the delivery element reacts with at least one reactive element on the guard element. The color change indicates that the delivery element is primed with the fluid.

Other features and advantages of the invention will become apparent from the following detailed description, taken in conjunction with the accompanying drawings which illustrate, by way of example, various features of embodiments of the invention.

BRIEF DESCRIPTION OF SEVERAL VIEWS OF THE DRAWINGS

A detailed description of embodiments of the invention will be made with reference to the accompanying drawings, wherein like numerals designate corresponding parts in the several figures.

DETAILED DESCRIPTION OF THE INVENTION

Figure 1:
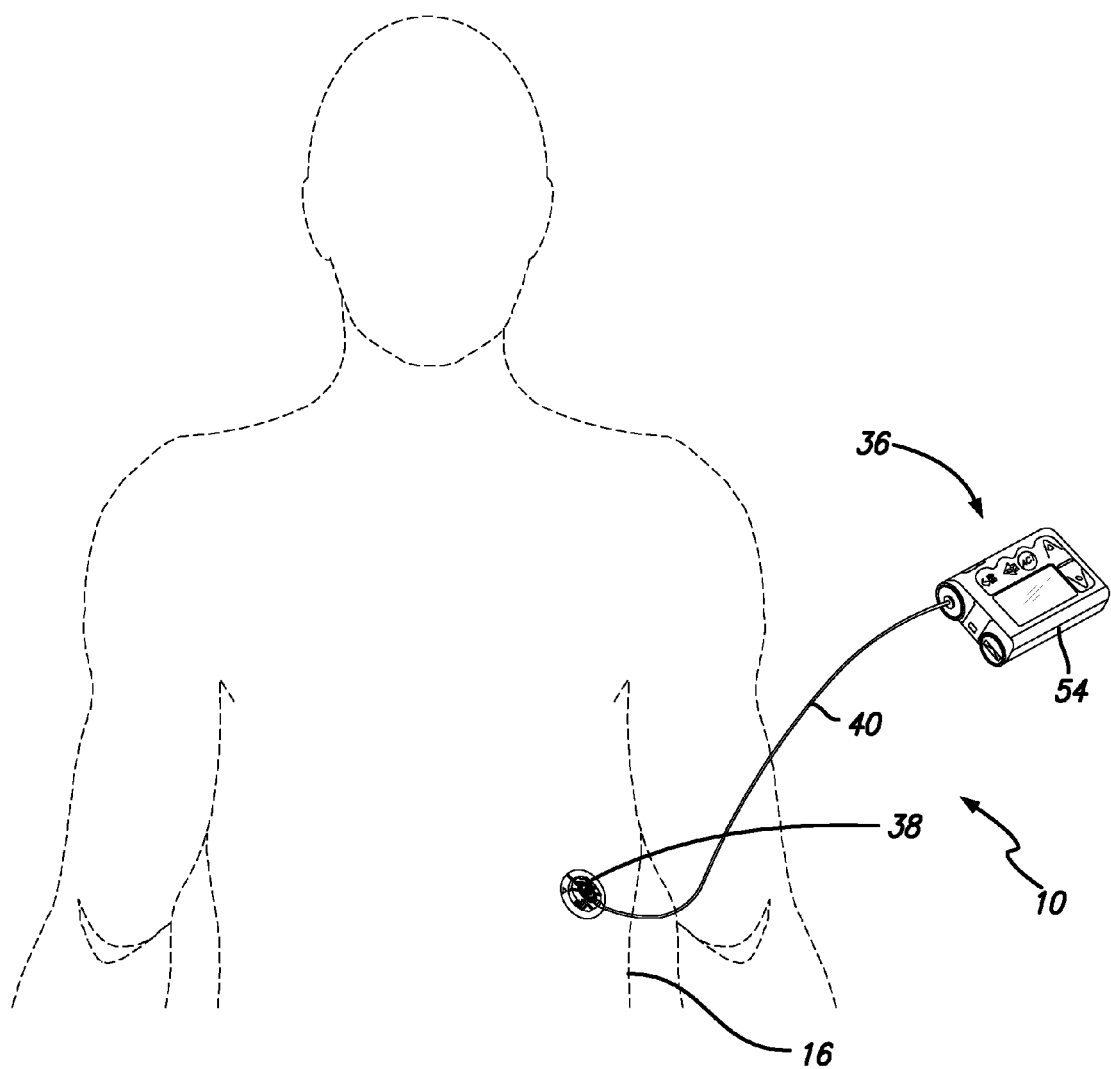
FIG. 1 is a diagram showing an infusion set attached to a body, a flexible tube, and an infusion pump according to an embodiment of the present invention.

As shown in the drawings for purposes of illustration, the invention is embodied in an infusion system having a priming detection system designed to indicate the presence of a fluid that has been primed through a fluid path of the infusion system for delivery of the fluid into an individual's body at an infusion site. The priming detection system includes at least one reactive element that reacts with the fluid or a component of the fluid to produce a color change. The provided color change is a clear indication that a component of the infusion system has been primed with the infusion fluid and is ready for use. The infused fluid can be any therapeutic agent. In preferred embodiments the infused fluid is insulin. However, many other fluids may be administered through infusion such as, but not limited to, HIV drugs, drugs to treat pulmonary hypertension, iron chelation drugs, pain medications, anti-cancer treatments, vitamins, hormones, or the like. Preferred embodiments are for use with human beings; however, alternative embodiments may be used with animals or fluid flow applications where detection of small amounts of primed fluid is important.

An infusion system 10 utilizing the priming detection method can include any or all of the components shown in FIG. 1. An infusion pump 36 regulates the flow of fluid into an individual's body. In embodiments, shown in FIG. 1, the fluid flows from an infusion pump 36, through a flexible tube 40, through a delivery device such as, an infusion set 38, or the like, and through a delivery element (not shown) that is adhered to the individual's body 16. Infusion sets 38 that may be used as a delivery device are described in, but not limited to, U.S. Pat. Nos. 5,176,662; 5,257,980; 5,584,813; 6,056,718; and 6,461,329, which are hereby incorporated by reference. The infusion pump 36 may be of the type described in U.S. Pat. Nos. 4,562,751; 4,685,903; 5,080,653; 5,097,122; 5,505,709; 6,248,093; 6,554,798; and 6,752,785, which are hereby incorporated by reference. Alternatively, other infusion pumps 36 may be used for delivery of fluid 14 through an infusion set 38 or through a delivery element to an individual's body 16.

Figure 2:
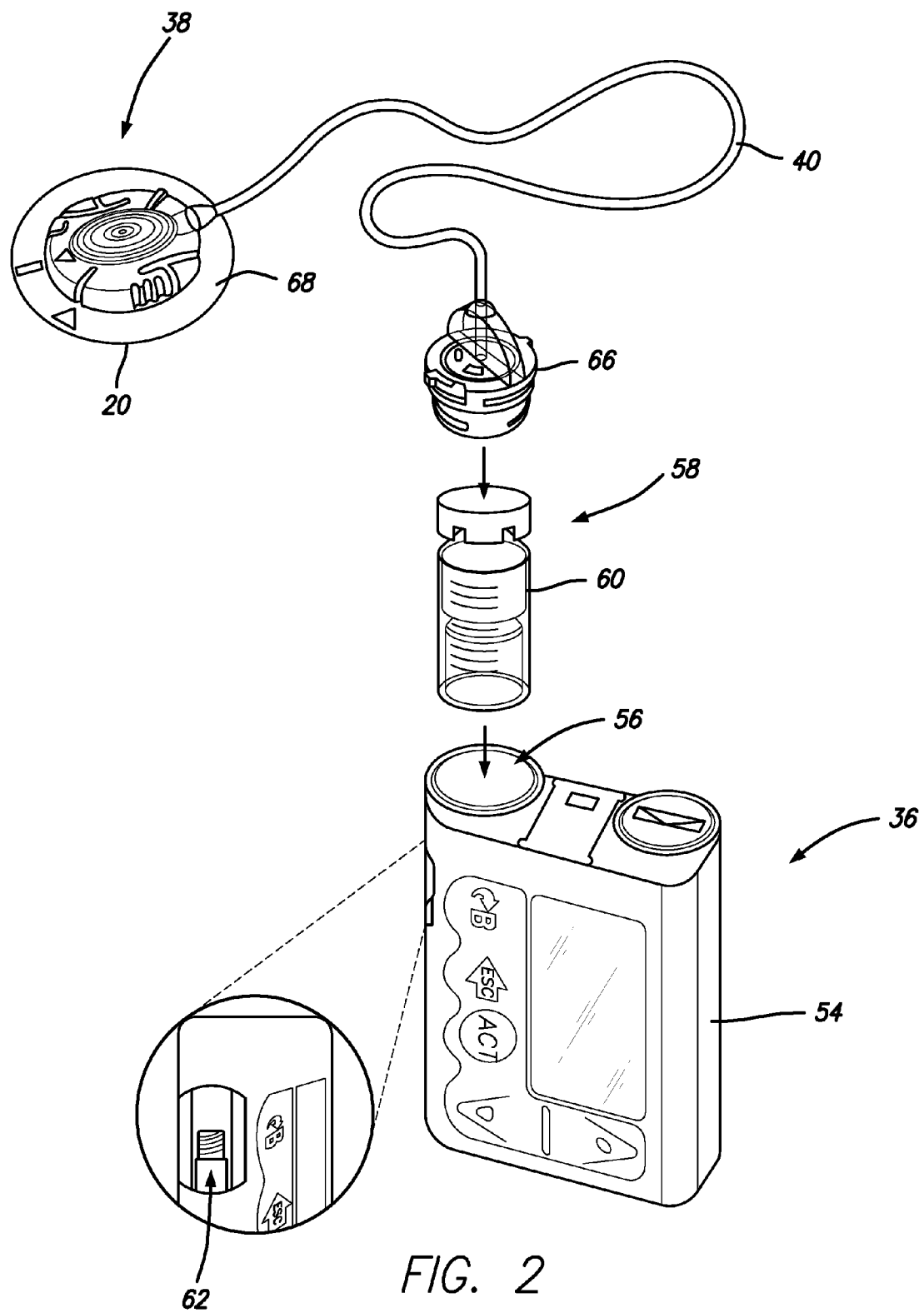
FIG. 2 is a perspective view of an infusion system according to an embodiment of the present invention.

An example embodiment of a system 10 utilizing an infusion pump 36 is shown in FIG. 2. In such embodiments, the infusion pump 36 comprises a relatively compact pump housing 54 defining an elongated reservoir compartment 56 adapted to receive a reservoir 58 filled with a selected fluid, such as medication to be administered to an individual. The reservoir 58 may be a fillable or pre-filled reservoir, cartridge, syringe or the like. The reservoir 58 includes a barrel 60 for containing the fluid 14. In embodiments, a connector 66 serves as the interface between the reservoir 58 and the tube 40. The infusion pump 36 can include electronics and a motor to control movement of a plunger 62 for advancing the reservoir 58 to deliver the fluid 14 through a flexible tube 40 or the like into an individual's body.

In operation, the fluid 14 flows along a normal fluid path from reservoir 58 seated within the infusion pump 36, through the flexible tube 40, through a delivery device, such as the infusion set 38 or the like, and exits through a delivery element 20, such as a cannula, hollow needle, capillary, conduit, lumen, or the like, to deliver the fluid 14 to an infusion site 12. The infusion site 12 is at a location where a delivery element 20 penetrates an individual's body. In embodiments, one end of the delivery element 20 is attached to a delivery device and the other end, once primed with the infusion fluid 14, is inserted through an individual's skin 74 terminating in an individual's subcutaneous tissue 76 or another tissue such as, muscle, organ, inter-peritoneal, intra-peritoneal, or the like. The delivery element 20 establishes fluid communication between the delivery device and the individual's body. In some embodiments the delivery device is an infusion set 38 coupled to the delivery element 20. In alternative embodiments, the delivery device can be an infusion pump 36 or other fluid source directly attached to the surface of the individual's skin 74 and having a delivery element 20.

Figure 3A:
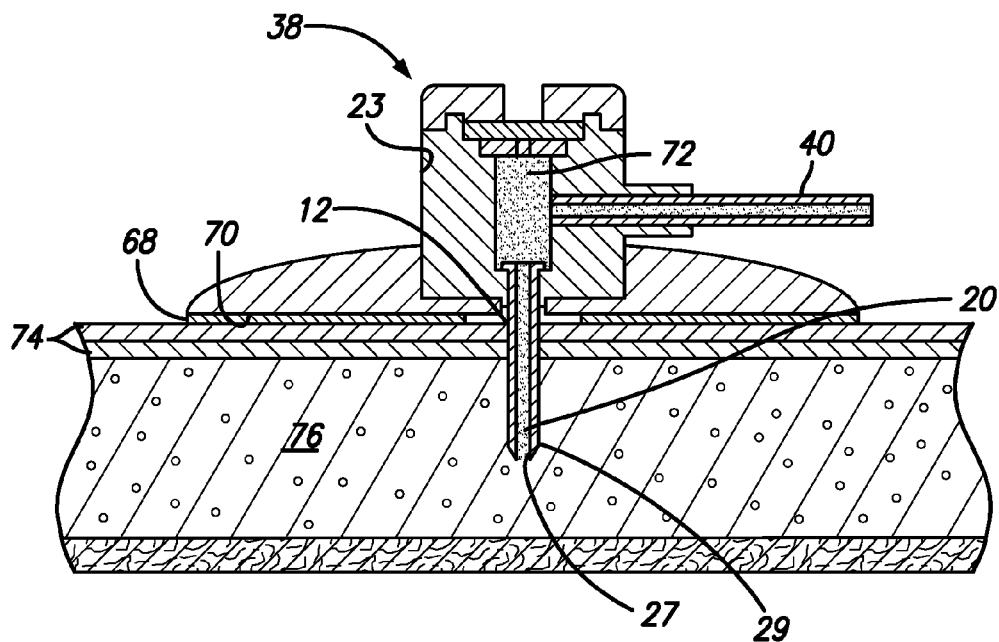
FIG. 3A is a cross-sectional side view of an infusion set attached to a body tissue according to an embodiment of the present invention.
Figure 3B:
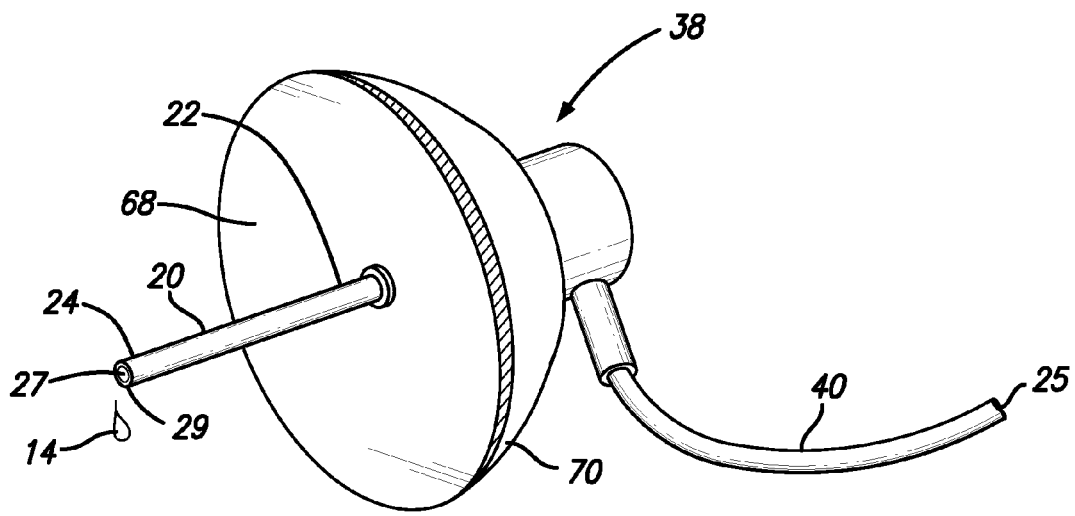
FIG. 3B is a perspective bottom view of the infusion set of FIG. 3A according to an embodiment of the present invention.
Figure 3C:
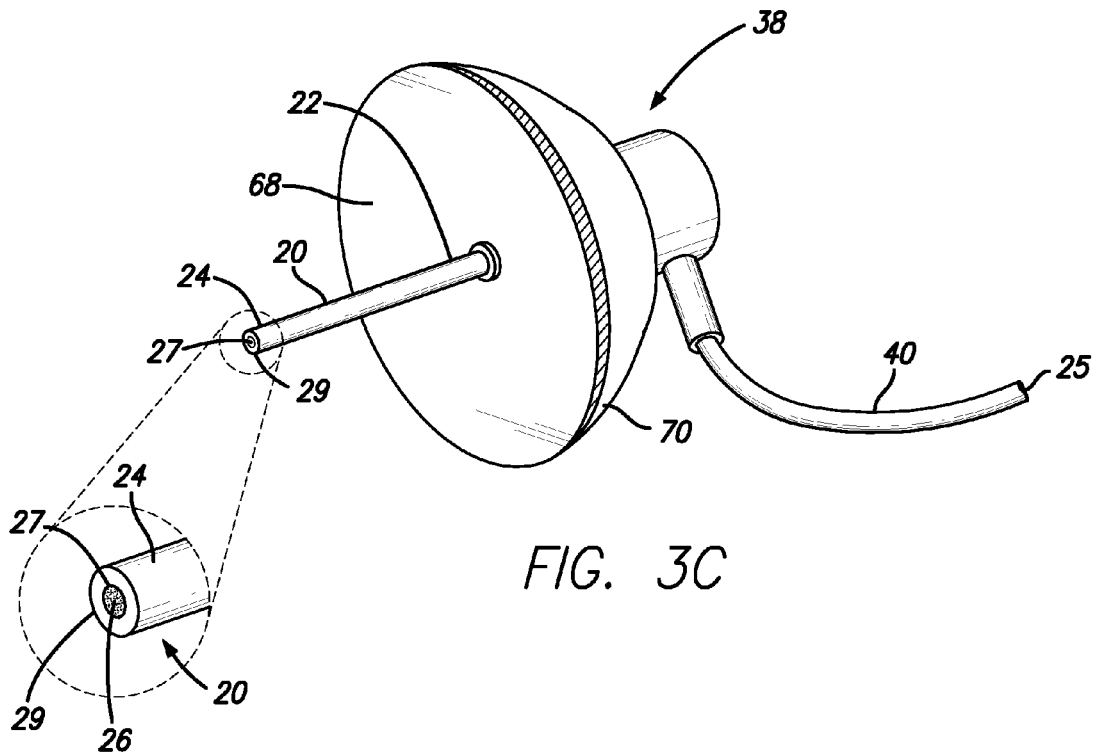
FIG. 3C is an enlarged front perspective view of a distal end of a delivery element having at least one reactive element deposited on at least a portion of the interior surface of the delivery element according to an embodiment of the present invention.
Figure 3D:
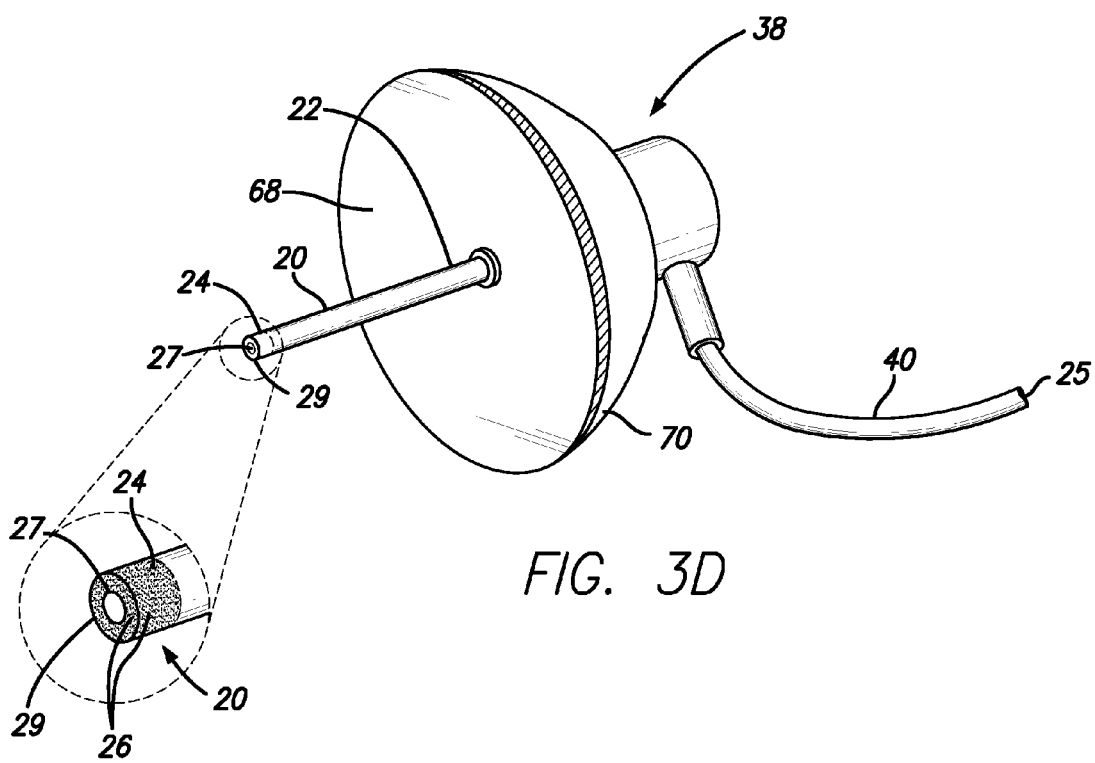
FIG. 3D is an enlarged front perspective view of a distal end of a delivery element having at least one reactive element deposited on at least a portion of the exterior surface of the delivery element according to an embodiment of the present invention.

As shown in embodiments in FIGS. 3A and 3B, the delivery element 20, such as a cannula or the like, directs the fluid 14 from a cavity 72 inside the infusion set 38, through the individual's skin, and into the individual's subcutaneous tissue 76. The characteristics of delivery element 20, such as the length, inner and outer diameter, end configurations, and materials may vary depending on the tissue type that the delivery element 20 is inserted into, the volume and type of fluid 14 being infused, the configuration of the delivery device, and other parameters. The delivery element 20 can include a proximal end 22 and a distal end 24. The distal end 24 is configured to penetrate the individual's body and the proximal end 22 is connected or coupled to the delivery device, thus providing fluid communication between the delivery device and the individual's body. A tube 40 may be included to connect the infusion set 38 to the infusion pump 36 or other fluid source (not shown).

In alternative embodiments, the delivery device is an infusion pump 36 adhered directly to the individual's skin 74. In a particular embodiment, shown in FIG. 4, the infusion pump 36 has a cannula as the delivery element 20, to deliver fluid 14 directly from the infusion pump 36 through the individual's skin 74 to the subcutaneous tissue 76. In particular embodiments, other fluid conducting delivery elements 20 are used such as capillaries, conduits, lumens, or the like. The infusion pump 36 may be of the type described in U.S. Pat. Nos. 4,902,278; 5,785,688; 5,814,020; 5,848,991; 5,858,001; 7,569,050; 7,641,649; 7,686,787; and 7,699,833; or other small disposable pumps for delivery of fluid 14 through a delivery element 20 to an individual's body.

Figure 4:
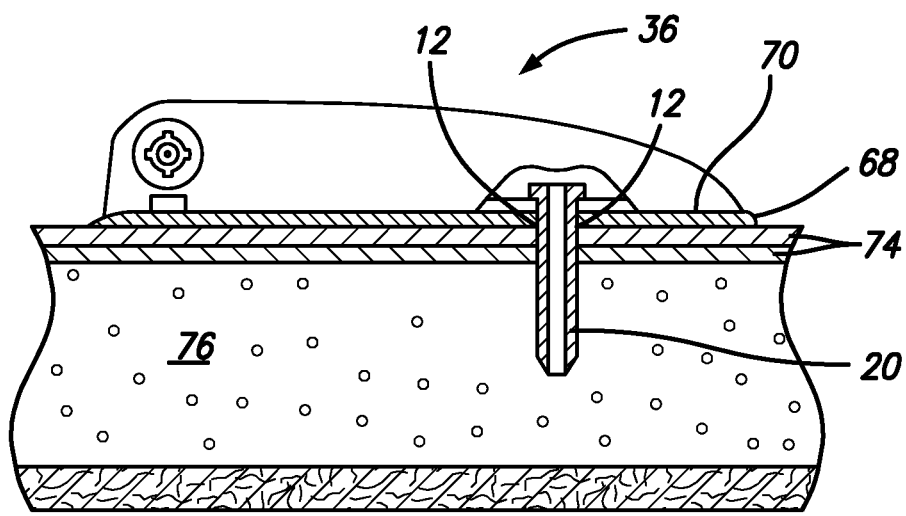
FIG. 4 is a side view of an infusion pump attached to a body tissue, with a partial cut away of the pump, showing a cross-sectional view of a delivery element penetrating the body tissue according to an embodiment of the present invention.

In some embodiments shown in FIGS. 2-4, the infusion pump 36 or infusion set 38 includes one or more pads 68 to attach the delivery device to the individual's skin 74. The pads 68 include an adhesive, and the pad 68 may be made of an adhesive, foam, glue, tape, a material coated with adhesive, or the like. As shown in the embodiments in FIG. 3A and FIG. 4, one side of the pad 68 can be attached to a base 70 of a delivery device, while the opposite side of the pad 68 can be adhered to an individual's skin 74. In other embodiments, the delivery device is held to the individual's skin 74 with a tape. In still other embodiments, both the adhesive of the pad 68 and tape are used to secure the infusion pump 36 or infusion set 38 to the individual's skin 74.

In the embodiments shown in FIGS. 5-13, a guard element 30 is included in the infusion system 10 and is configured to at least partially surround or cover at least a portion any of the above-described delivery elements 20, preferably the distal end of a delivery element 20. In some embodiments, the guard element 30 can be a needle guard, cap, lid, top, cover, or the like. The guard element 30 can have a first end 31 and a second end 33. In embodiments, at least one of the first end 31 and second end 33 of the guard element 30 can connect to the delivery device having the delivery element 20. In some embodiments, the guard element 30 and delivery device such as an infusion set can have mating or interfitting parts such as male and female threaded or snapping counterparts or the like to connect the guard element 30 to the delivery device. In an embodiment shown in FIG. 5, the guard element 30 comprises an elongated body 46 having a first end 31 that is an open end 50 to accept the delivery element 20 and a second end 33 that is a closed end 48 to enclose at least a portion of the delivery element 20. The guard element 30 can be made of a plastic or polymeric material, non-fiber material, fiber material or the like. The guard element 30 can be made of a rigid material to shield the user from the sharp distal end of a delivery element 20, such as a needle, and to further block contaminants from reaching the delivery element 20 to keep the delivery element 20 sterile.

In preferred embodiments, the fluid detection portion of the infusion system 10 that indicates when a component of the infusion system 10 is primed includes at least one reactive element 26 that changes color upon contact with the fluid 14 to be delivered to the user's body. The reactive element 26 or reactants may be deposited on the surfaces of the components, such as the guard element 30, the delivery element 20, the infusion set 38, and/or the tube 40, by different methods. In embodiments, the reactive element 26 can be sprayed, coated, deposited, layered or screened directly onto at least a portion of the surface of one or more of the components. In alternative embodiments, the reactive element 26 can be encapsulated in micro-spheres or included as a component of a material such as a gel, an absorbent material, foam, porous materials, starch granules, or the like, which are applied to at least a portion of the surface of one or more of the components.

In yet further embodiments, the reactive element 26 can be embedded in or otherwise incorporated in at least a portion of one or more components of the infusion system 10. The reactive element 26 can be applied to or incorporated into fabric materials, non-fabric materials, plastic or polymeric materials, fibrous materials, foam, porous materials, or the like, or other materials that wick away fluid to accelerate the reaction or make the resulting product of the reaction more visible and easily observable to the user. In embodiments, the reactive element can be embedded in pockets of such materials.

In further embodiments, the reactive element 26 can be sprayed, coated, deposited, layered or screened onto a layer that is applied to at least a portion of the surface of one or more of the components. The layer can be made of hydrogel, cloth, fibrous material, porous material, or other materials that wick away fluid to accelerate the reaction or make the resulting product of the reaction more visible. In further alternative embodiments, a label of any suitable flexible material may be prepared with the reactants on one or both sides of the label, and the label may be applied onto a surface of the guard element 30, the delivery element 20, the infusion set 38, and/or the tube 40.

Figure 5:
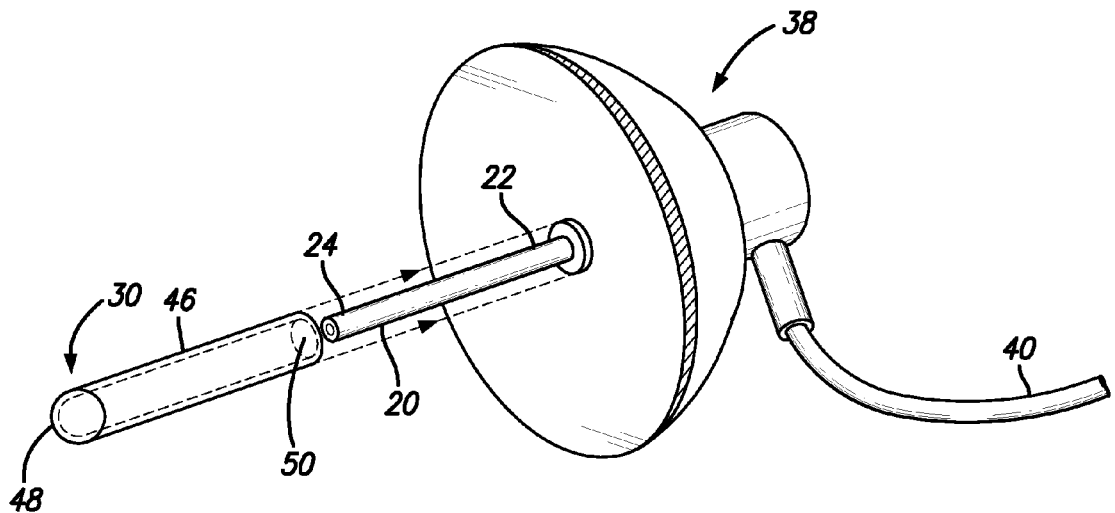
FIG. 5 is a perspective bottom view of an infusion set and a perspective view of a guard element according to an embodiment of the present invention.
Figure 6:
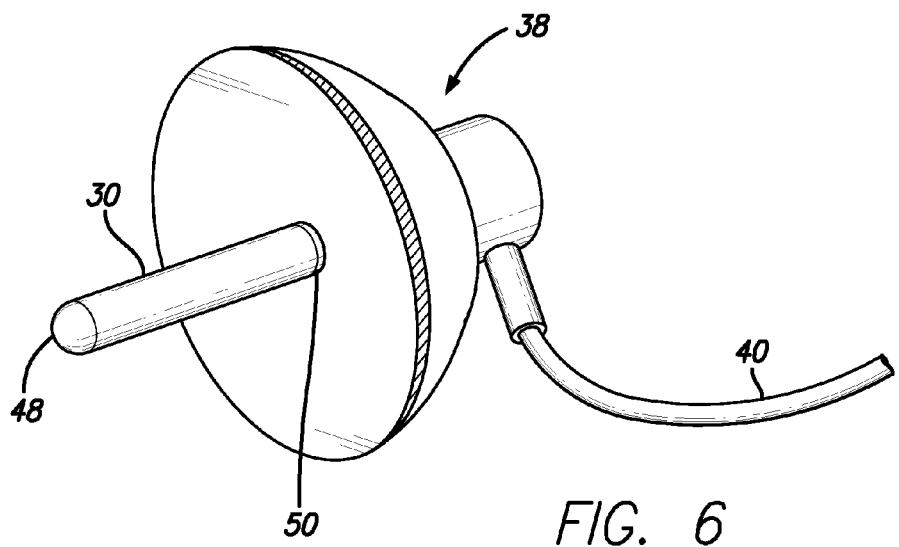
FIG. 6 is a perspective bottom view of an infusion set and a perspective view of a guard element covering a delivery element according to an embodiment of the present invention.
Figure 7:
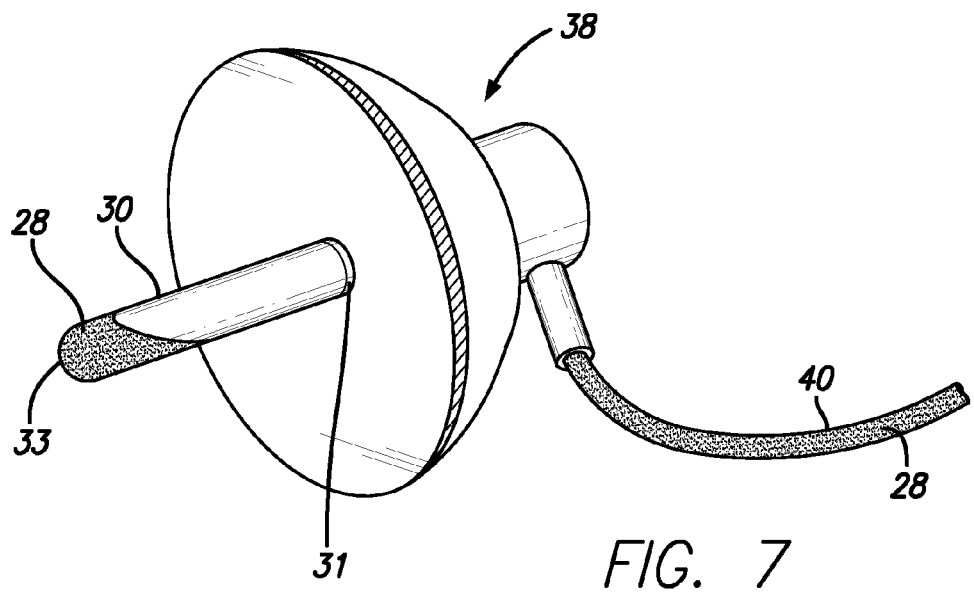
FIG. 7 is a perspective bottom view of an infusion set and a perspective view of a guard element covering a delivery element and showing a color change to indicate the delivery element is primed according to an embodiment of the present invention.

As shown in embodiments in FIGS. 5 and 6, the guard element 30 covers the delivery element 20 such that the interior surface 32 of the guard element 30 faces the delivery element 20. Once the fluid 14 has traveled along the normal fluid path of the system from the delivery device and through the delivery element 20, the fluid 14 will exit the distal end of the delivery element 20 and come into contact with the guard element 30 covering the delivery element 20, and thus come into contact with the reactive element 26 coated on or incorporated in at least a portion of the guard element 30. As illustrated by the embodiment shown in FIG. 7, the reactive element 26 will produce a color change 28 that indicates that the system is primed through the delivery element 20 and is ready for insertion at the infusion site 12.

Figure 8:
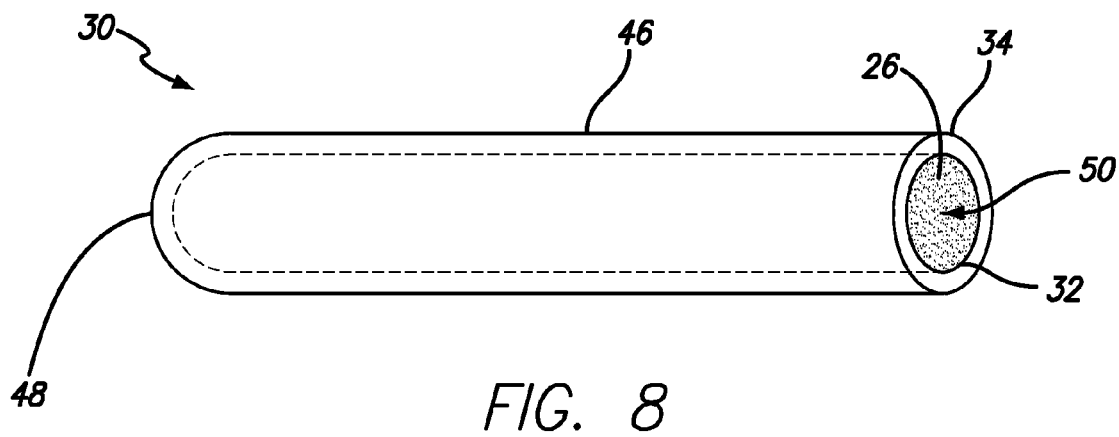
FIG. 8 is a perspective side view of a guard element having at least one reactive element deposited on the interior surface of the guard element according to an embodiment of the present invention.
Figure 9:
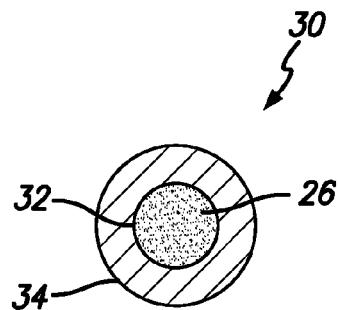
FIG. 9 is a front view of an open end of a guard element having at least one reactive element deposited on at least a portion of the interior surface of the guard element according to an embodiment of the present invention.
Figure 10:
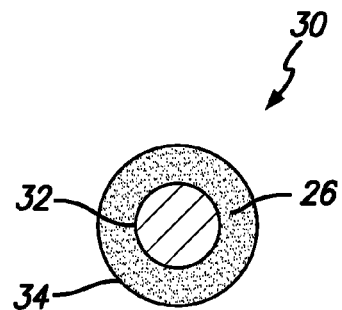
FIG. 10 is a front view of an open end of a guard element having at least one reactive element incorporated in at least a portion of the guard element according to an embodiment of the present invention.

In embodiments shown in FIGS. 8 and 9, the guard element 30 has an interior surface 32 and an exterior surface 34, and the reactive element 26 is deposited or coated on a portion of or the entire interior surface 32 within the guard element 30. Alternatively, the reactive element 26 is deposited or coated in a layer that is applied to the interior surface 32 of the guard element 30. In an alternative embodiment shown in FIG. 10, the reactive element 26 is incorporated into the body of the guard element 30. For example, the guard element 30 can be made of a sintered plastic that absorbs liquid, a rigid fiber material, or other suitable material that can incorporate the reactive element 26. Further, the reactive element 26 may be deposited on a wicking material incorporated in or deposited on the interior surface 32 of the guard element to make the color change 28 easier to observe by the user. For example, the wicking material may draw the leaking fluid 14 toward the exterior surface of the guard element. In preferred embodiments, the guard element 30, or other component of the system utilizing the reactive element, is clear or transparent to increase visibility of the color change 28. In some embodiments, the guard element 30, or other component of the system utilizing the reactive element, may be comprised of a translucent material that allows color to be seen through the translucent material.

Figure 11:
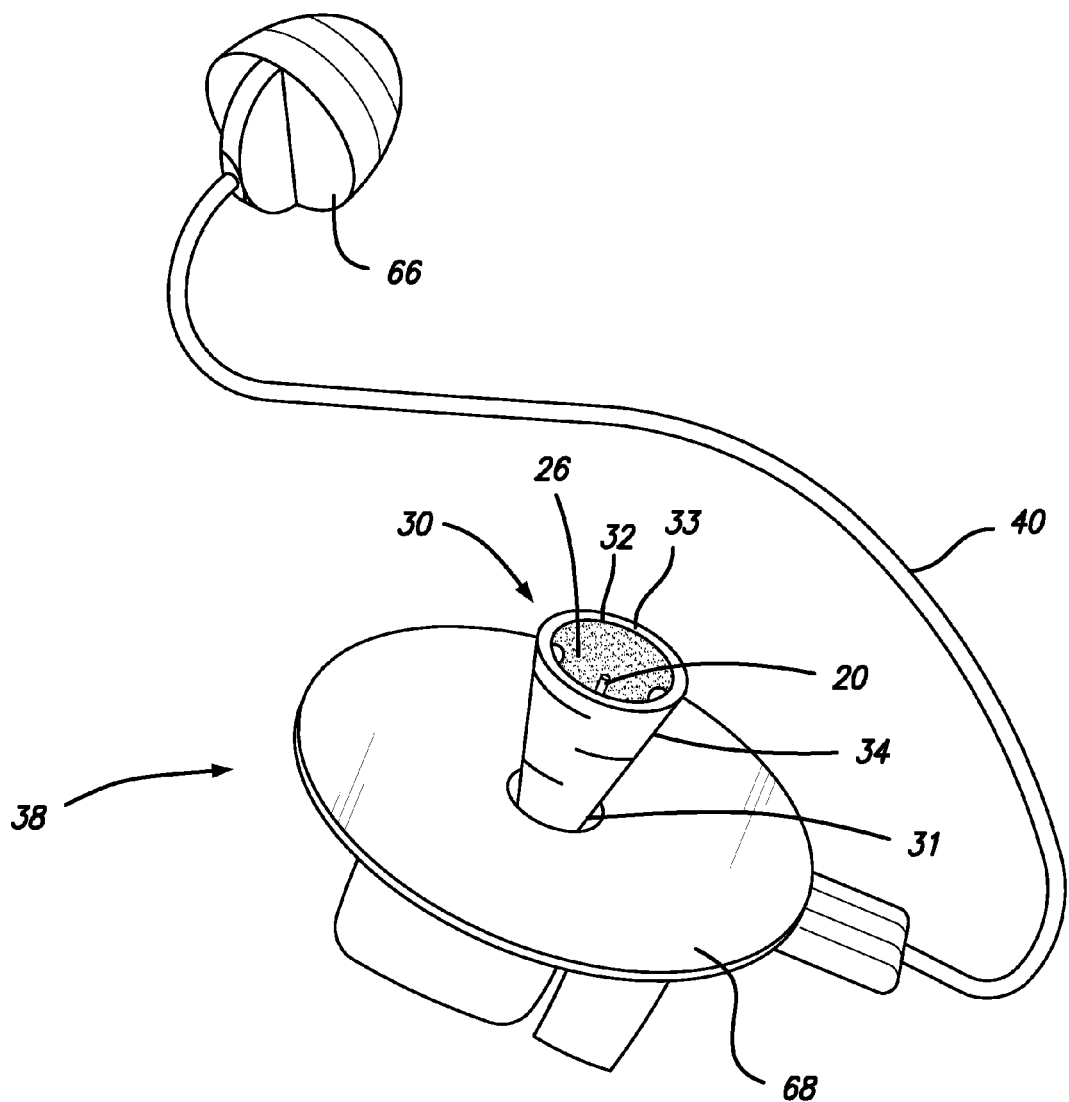
FIG. 11 is a perspective bottom view of an infusion set and a perspective view of a guard element surrounding a delivery element according to an embodiment of the present invention.
Figure 12:
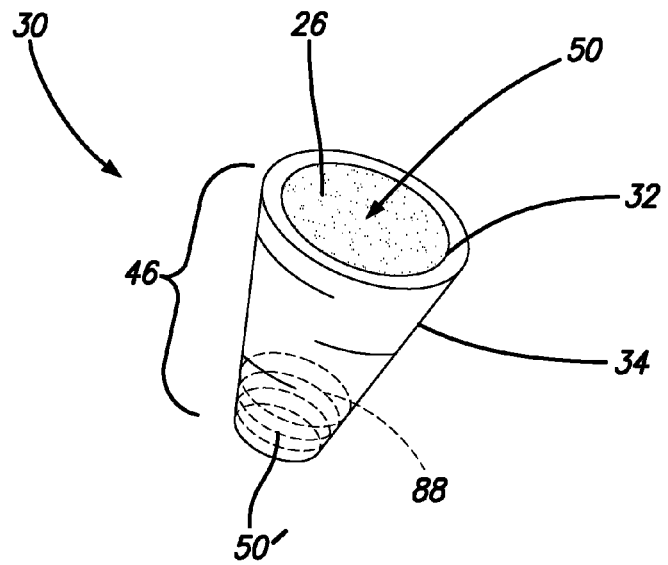
FIG. 12 is a perspective side view of a guard element having at least one reactive element deposited on the interior surface of the guard element according to an embodiment of the present invention.
Figure 13:
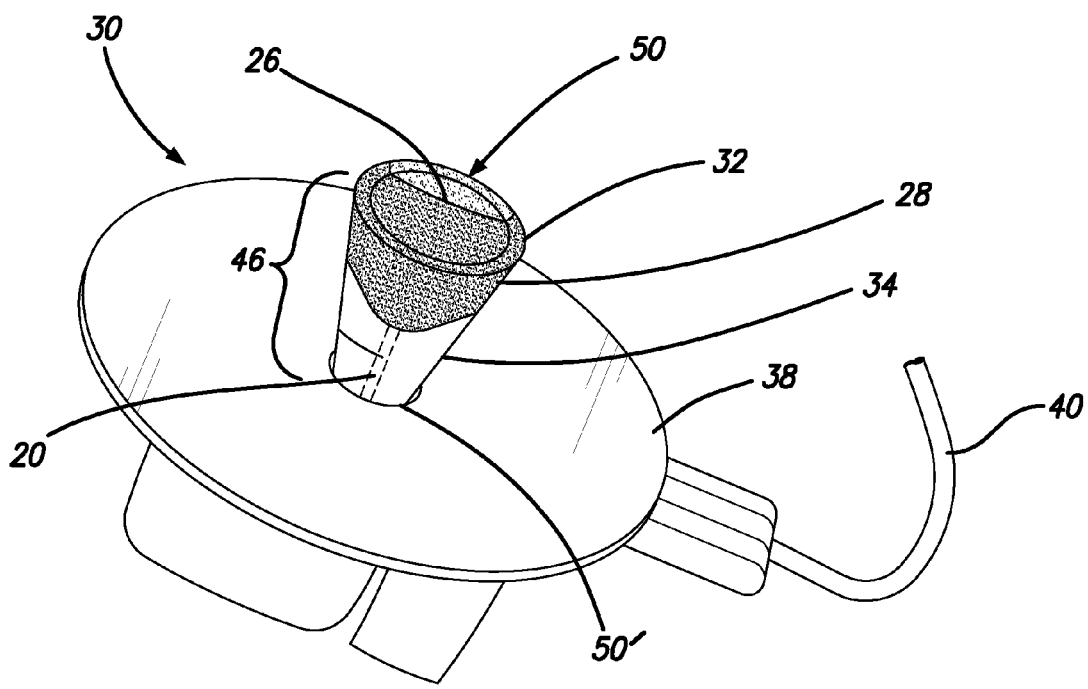
FIG. 13 is a perspective bottom view of an infusion set and is a perspective view of a guard element surrounding a delivery element and showing a color change to indicate the delivery element is primed according to an embodiment of the present invention.

In alternative embodiments shown in FIGS. 11-13, the guard element 30 can have a body 46 with a first end 31 and a second end 33. As illustrated in the embodiments of FIGS. 11-13, the first end 31 and second end 33 can comprise two open ends 50 and 50'. In embodiments having two open ends 50 and 50', the guard element 30 can surround the delivery element 20 and have a body 46 that extends past the delivery element 20. In embodiments, at least the first end 31 or the second end 33 of the guard element 30 can connect with a delivery device to surround the delivery element 20. For example, one open end 50' of the guard element 30 and a portion of the delivery device such as an infusion set to which the open end 50' connects can have mating or interfitting parts 88 such as male and female threaded or snapping counterparts or the like to connect the guard element 30 to the delivery device.

As shown in the embodiment in FIG. 11, the guard element 30 surrounds the delivery element 20 such that one end of the guard element 30 is attached to the delivery device and the interior surface 32 of the guard element 30 faces the delivery element 20. Once the fluid 14 has traveled along the normal fluid path of the system from the delivery device and through the delivery element 20, the fluid 14 will exit the distal end of the delivery element 20 and come into contact with the guard element 30 surrounding the delivery element 20, and thus come into contact with the reactive element 26 coated on or incorporated in at least a portion of the guard element 30. For example, the fluid 14 may drip down or to the side of the delivery element 20 to come into contact with at least a portion of the interior surface 32 of the body 46 of the guard element 30. As illustrated by the embodiment shown in FIG. 13, the reactive element 26 will produce a color change 28 that indicates that the system is primed through the delivery element 20. The user can then remove the guard element 30 from the delivery device, such as an infusion set 38, for insertion of the delivery element 20 into an individual's body.

In further alternative embodiments, the reactive element 26 may be deposited on at least a portion of the interior surface 23 of the infusion set 38 or interior surface 25 of the tube 40 that are wetted by the fluid 14 when the fluid 14 flows along the normal fluid path of the system. In yet further embodiments, the reactive element 26 can be deposited on at least a portion of the delivery element 20. For example, as shown in the embodiment in FIG. 3C, the reactive element 26 may be coated on an interior surface 27 of the delivery element 20. The entire interior surface 27 or a portion of the interior surface 27 of the delivery element 20 can be coated. In alternative embodiments, the reactive element 26 can be deposited at the exit on the edge of the distal end on the exterior surface 29 of the delivery element 20, as shown in an embodiment in FIG. 3D. The entire exterior surface 29 or a portion of the exterior surface 29 of the delivery element 20 can be coated. Embodiments utilizing the reactive element 26 that contact the fluid 14 to be infused along a fluid flow path of the system can use one or more reactive elements 26 that are safe for use in the individual's body so as not to harm the individual. As the fluid 14 flows along a normal path of the system from the tube 40, through the infusion set 38, and through the delivery element 20, one or all of the components utilizing the reactive element 26 will produce a color change 28 to indicate that the component is primed with the infusion fluid 14. In embodiments, the components of the system utilizing the color-changing reactive element may include other clear (optically transparent or translucent) materials for the individual to see through the component and observe the reaction.

In certain embodiments, the reactive element 26 can be a liquid-activated dye. The dye or ink can reversibly and irreversibly change from a first color to a second color when exposed to water. Upon contact with a fluid 14 or liquid, for example water or a fluid containing water, the dye can change from a first color to a second color when wet and remain the second color when dry, or change back to the first color when dry. The color can change from a dark color to a light color, a light color to a dark color, become transparent, or change from and to any color of the rainbow and shades in between, including white and black. As non-limiting examples, the liquid-activated dyes can be reversible or irreversible hydrochromatic or hydrochromic inks or coatings or the like. The first and second colors can be adjusted based on the hydrochromatic or hydrochromic molecules used in the dyes that are known to persons having ordinary skill in the art.

In embodiments, the reactive dye can react with at least one component within the fluid 14. For example, in embodiments where the fluid 14 to be delivered into an individual's body includes a protein, such as an insulin formulation, other reactive elements may be used to produce a color change 28. In particular embodiments, either ninhydrin or Coomassie Brilliant Blue reacts with the protein in the fluid 14 resulting in a brightly colored product. Other color-changing chemicals or dyes specific to the infused fluid 14 or a known component of the infused fluid 14, such as a protein, hormone, or other like component, can be used. In some embodiments, the at least one reactive element 26 can be a colorimetric protein assay reagent or chemical that reacts with a component of the fluid 14 to be delivered. For example, the reagent can be a dye that binds to a protein or a portion of a protein complex such that the color change 28 is directly or indirectly associated with the bound dye. In addition to indicating presence of the fluid-containing protein, the color change 28 in such embodiments can indicate the amount or strength of the protein in the fluid 14.

Figure 14:
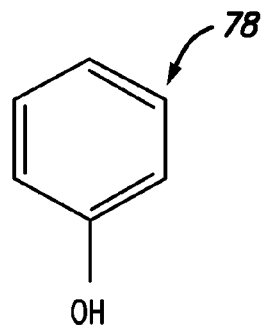
FIG. 14 is a diagram of a phenol molecule.
Figure 15:
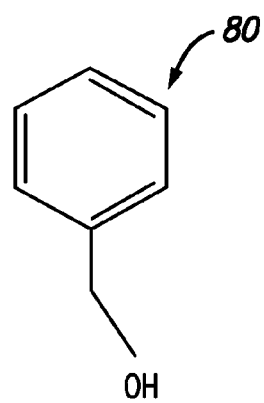
FIG. 15 is a diagram of a benzyl alcohol molecule.

In some embodiments of the present invention, the reactive element 20 includes a chemical that reacts with preservatives in the infusion fluid 14 to generate a highly visible, brightly colored, chemical complex. Most fluids designed for parenteral administration (and/or infusion) contain a preservative. The most commonly used preservatives are based either on a phenol system 78 or a benzyl alcohol system 80. Examples of these systems are shown in FIGS. 14 and 15 respectively. Thus, one approach to detecting the fluid is to trigger a chemical reaction that is observable by an individual when any of these preservatives are present in a fluid.

Figure 16:
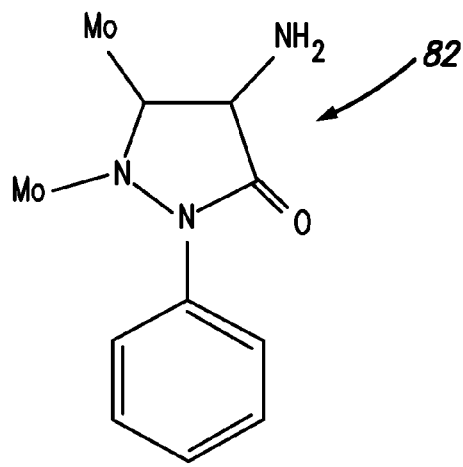
FIG. 16 is a diagram of a 4-amino-antipyrine molecule.
Figure 17:
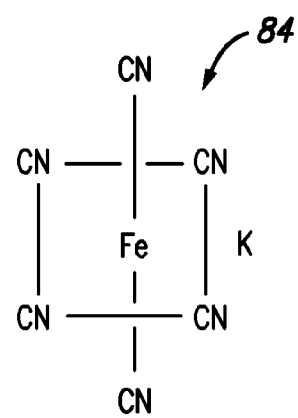
FIG. 17 is a diagram of a potassium ferricyanide (K3Fe(CN)6 molecule.
Figure 18:
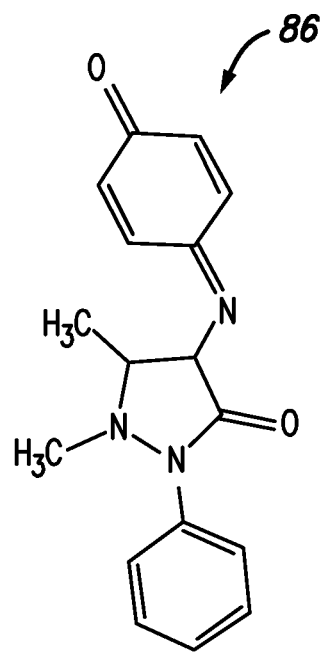
FIG. 18 is a diagram of a bright blue chemical complex.

In embodiments, a material, for example a clear gel, containing 4-amino-antipyrine 82, shown in FIG. 16, and potassium ferricyanide 84 (K3Fe(CN)6), shown in FIG. 17, is deposited on at least a portion of the surface of a component of the system. When fluid 14 contacts the reactive element 26, the preservative in the parenteral fluid reacts with the 4-amino-antipyrine 82 and potassium ferricyanide 84 in the material. The resulting product is a bright blue colored complex 86. Thus, the reactive elements, seen on, through, or around the edges of a component of the system, change from clear to bright blue, serving as a visual indicator to the individual. A drawing of the structure of the resulting bright blue colored complex 86 is shown in FIG. 18. The time required for detection may vary due to the concentrations of the reactants, 4-amino-antipyrine 82 and potassium ferricyanide 84, the concentration of the preservative in the fluid, the flow rate of the fluid, the rate at which the fluid comes in contact with the reactants, the method used to deposit the chemicals, the temperature, and the presence of contaminants. In alternative embodiments, the clear gel may be some other color, such as white, cream, off white, or the like, or a contrasting color to make the color change 28 noticeable. In other embodiments, the colored product is a different color, such as red, yellow, orange, pink, green, purple, or the like.

In alternative embodiments, an enzymatic system is used to amplify the chemical color change 28 signal. An enzyme, such as horse radish peroxidase (HRP), is added to the material containing 4-aminoantipyrine 82 and potassium ferricyanide 84. When a fluid 14 reaches the enzyme, water in the fluid 14 dissolves the HRP. The HRP then acts as a catalyst to, in essence, create an enzymatic amplification of the signal. Again, a deep blue colored complex 86 is formed due to the phenol 78 or benzyl alcohol 80 preservatives in the fluid 14 reacting with 4-aminoantipyrine 82 and potassium ferricyanide 84. The advantage of the HRP system is that only very small amounts of the fluid 14 need to be present to be detected. In alternative embodiments, the time required to detect the fluid 14 can vary depending on the concentration of HRP present in the gel, the concentration of the reactants 4-aminoantipyrine 82 and potassium ferricyanide 84, the method used to deposit the chemicals, the rate that the fluid 14 spreads and comes in contact with the reactants, the temperature, and the concentration of contaminates. The catalysts described above, which amplify the color change 28 from the chemical reaction, may also be deposited on a surface of a component of the system, such as the guard element 30, tubing 40, infusion set 38, or delivery element 20 of the system 10.

Figure 19:
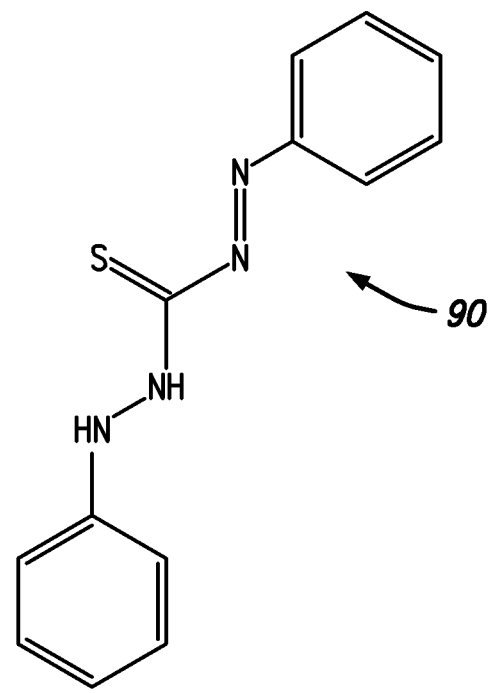
FIG. 19 is a diagram of a dithizone molecule.

In another embodiment of the present invention, the reactive element 20 includes a chemical that reacts with zinc in an infusion fluid 14 to generate a color change. A drawing of the structure of an example molecule, dithizone 90, is shown in FIG. 19. Thus, one approach to detecting the fluid is to trigger a chemical reaction that is observable by an individual when zinc is present in a fluid. As a non-limiting example, the infusion fluid 14 can be insulin. Insulin formulations can include zinc that will react with the dithizone molecule 90 to produce a color change. Dithizone 90 can be incorporated in or deposited, coated, or the like, on a component of the infusion system 10 to indicate the component is primed.

In further alternative embodiments, the reactive elements 20 such as dithizone 90, 4-aminoantipyrine 82 and/or potassium ferricyanide 84 are encapsulated in micro-spheres. In particular embodiments, the micro-spheres dissolve in the presence of an ingredient contained in the infused fluid 14, such as water, alcohol, insulin or the like, which then sets the reactants free to react with the preservative in the fluid 14 as described above. Additional embodiments include HRP encapsulated in micro-spheres along with 4-aminoantipyrine 82 and potassium ferricyanide 84. In other embodiments, different methods are employed. These methods include applying the reactive elements with starch granules, depositing them in pockets formed in a component of the system, such as the guard element 30, encapsulating them and mixing them with a gel, embedding them into a component of the system, or the like.

Different methods for determining when a component of an infusion system is primed with a fluid to be delivered into an individual's body can be ascertained from the aforementioned embodiments of the invention described herein. For example, in one embodiment, the method comprises: providing the fluid and a device for delivering the fluid into the individual's body; providing the delivery element having a proximal end and a distal end, the distal end configured to penetrate the individual's body and the proximal end connected to the delivery device; providing a guard element to cover at least the distal end of the delivery element; depositing at least one reactive element that reacts with the fluid on the guard element; and producing and/or observing a color change when the fluid exiting from the distal end of the delivery element reacts with the at least one reactive element, thereby indicating that the delivery element is primed with the fluid.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An infusion system having at least one reactive element to indicate a component of the infusion system is primed with a fluid to be delivered into an individual's body, the infusion system comprising:
    a delivery device for attaching directly to and delivering the fluid into the individual's body, wherein the delivery device is an infusion pump or an infusion set;
    a delivery element having a proximal end and a distal end, the distal end configured to penetrate the individual's body and the proximal end connected to and not removable from the delivery device, to provide fluid communication between the delivery device and the individual's body, wherein the delivery element is a cannula or a needle;
    wherein the at least one reactive element is provided directly on at least a portion of a surface of the delivery element;
    wherein the fluid is a therapeutic agent and the therapeutic agent is insulin; and
    the at least one reactive element reacts with the insulin when the insulin contacts the at least one reactive element to produce a color change on at least the portion of the surface of the delivery element, wherein the color change indicates that the delivery element of the infusion system is primed with the insulin.

2. The infusion system of claim 1, further including a guard element to cover at least a portion of the delivery element, wherein the at least one reactive element is further provided on the guard element and reacts with the insulin exiting from the delivery element to further produce the color change on the guard element to indicate that the delivery element is primed with the insulin.

3. The infusion system of claim 2, the guard element having an interior surface and an exterior surface, wherein the at least one reactive element is provided on at least a portion of the interior surface of the guard element.

4. The infusion system of claim 2, the guard element configured to surround at least a portion of the delivery element, the guard element having an interior surface facing the delivery element, a first end and a second end comprising two open ends, wherein the first end removably connects with the delivery device and the second end extends past the distal end of the delivery element; and
    the interior surface of the guard element including the at least one reactive element that reacts with the insulin exiting from the distal end of the delivery element to produce the color change to indicate that the delivery element is primed with the insulin.

5. The infusion system of claim 4, wherein the first end of the guard element and the delivery device include mating parts to removably connect with one another.

6. The infusion system of claim 1, wherein the at least one reactive element is provided on an interior surface of the delivery element.

7. The infusion system of claim 1, wherein the delivery device is an infusion set.

8. The infusion system of claim 7, the infusion system further including an infusion pump and a tube coupled between the infusion set and the infusion pump.

9. The infusion system of claim 8, wherein the at least one reactive element is provided within at least a portion of the tube.

10. The infusion system of claim 1, wherein the at least one reactive element is provided on an exterior surface of an edge of the distal end of the delivery element.

11. The infusion system of claim 1, wherein the at least one reactive element includes a liquid-activated dye to produce the color change.

12. The infusion system of claim 1, wherein the at least one reactive element includes a chemical that reacts with at least one component within the insulin to produce the color change.

13. The infusion system of claim 1, wherein the at least one reactive element contains at least 4-amino-antipyrine and potassium ferricyanide.

14. The infusion system of claim 1, wherein the at least one reactive element contains at least 4-amino-antipyrine, potassium ferricyanide and horse radish peroxidase (HRP).

15. The infusion system of claim 1, wherein the at least one reactive element contains at least ninhydrin.

16. The infusion system of claim 1, wherein the at least one reactive element contains a hydrochromatic molecule.

17. The infusion system of claim 1, wherein the at least one reactive element contains at least dithizone.

18. A method for determining when a delivery element of an infusion system is primed with a fluid to be delivered into an individual's body, the method comprising:
    providing a delivery device for attaching directly to and delivering the fluid into the individual's body, wherein the delivery device is an infusion pump or an infusion set, and wherein the fluid is a therapeutic agent and the therapeutic agent is insulin;
    providing the delivery element having a proximal end and a distal end, the distal end configured to penetrate the individual's body and the proximal end connected to and not removable from the delivery device, wherein the delivery element is a cannula or a needle;
    providing at least one reactive element directly on at least a portion of a surface of the delivery element; and
    producing a color change on at least the portion of the surface of the delivery element when the insulin reacts with the at least one reactive element, thereby indicating that the delivery element is primed with the insulin.

19. An infusion system having at least one reactive element to indicate a component of the infusion system is primed with a fluid to be delivered into an individual's body, the infusion system comprising:

a delivery device for attaching directly to and delivering the fluid into the individual's body, wherein the delivery device is an infusion set;

a delivery element having a proximal end and a distal end, the distal end configured to penetrate the individual's body and the proximal end connected to and not removable from the infusion set, to provide fluid communication between the infusion set and the individual's body;

the infusion set having a cavity to provide fluid communication through the infusion set between the delivery element and a fluid source;

wherein the at least one reactive element is provided on at least a portion of an interior surface of the infusion set facing the cavity; and the at least one reactive element reacts with the fluid when the fluid contacts the at least one reactive element to produce a color change on at least the portion of the interior surface of the infusion set, wherein the color change indicates that the infusion set of the infusion system is primed with the fluid.

* * * * *